United States Patent [19]

Shipko

[11] 4,141,752
[45] Feb. 27, 1979

[54] ORGAN-STIMULATING APPARATUS AND INSULATING SET SCREW FOR SUCH APPARATUS

[75] Inventor: Frederick J. Shipko, Spring Church, Pa.

[73] Assignee: Coratomic, Inc., Indiana, Pa.

[21] Appl. No.: 817,820

[22] Filed: Jul. 21, 1977

[51] Int. Cl.² .............................................. A61N 1/02
[52] U.S. Cl. ................................................ 128/419 P
[58] Field of Search ........ 128/419 P, 419 PG, 419 PS

[56] References Cited
U.S. PATENT DOCUMENTS 3,908,668  9/1975  Bolduc ........................... 128/419 P
4,010,760  3/1977  Kraska et al. .................... 128/419 P Primary Examiner—William E. Kamm
Attorney, Agent, or Firm—Hymen Diamond

[57] ABSTRACT

Organ-stimulating apparatus in which the catheter extends through a threaded cavity or socket and is held by an electrically insulating set screw that is screwed into the cavity and seals the cavity against the penetration of body fluids. The set screw includes a threaded member which extends from an insulating head. An O-ring extends around the periphery of the head and when the set-screw is screwed into the threaded member, the O-ring engages the wall of the cavity sealing the cavity against the penetration of body fluids.

8 Claims, 10 Drawing Figures

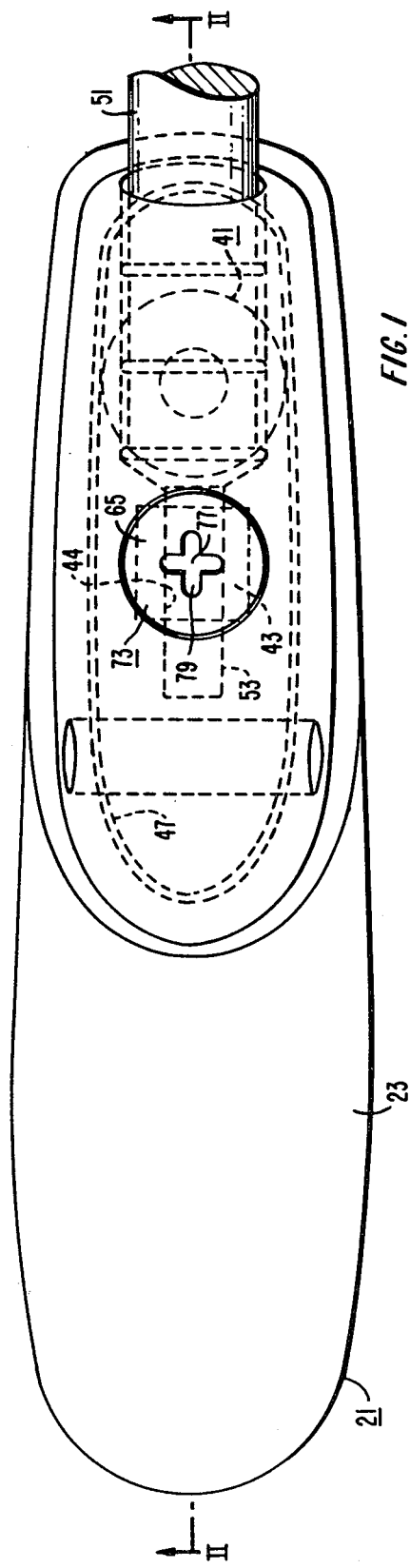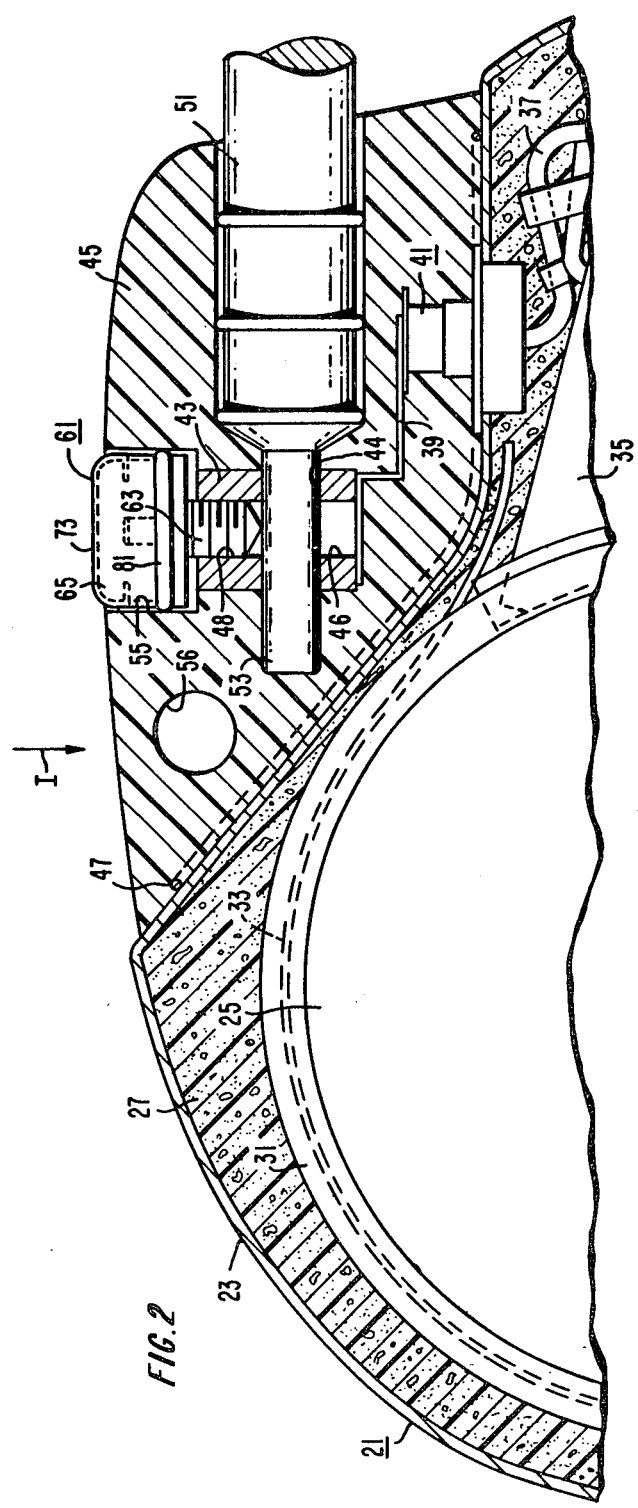

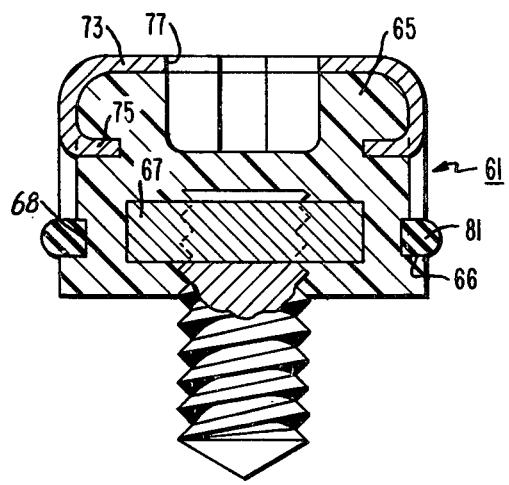
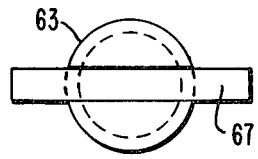
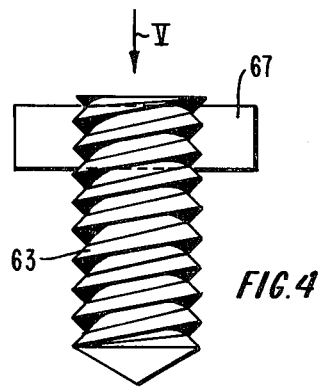
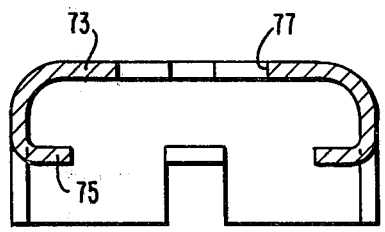
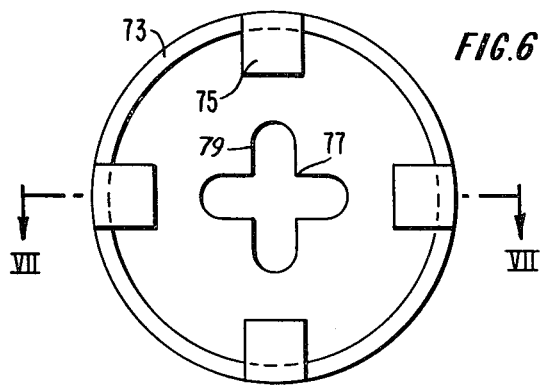

ORGAN-STIMULATING APPARATUS AND INSULATING SET SCREW FOR SUCH APPARATUS

BACKGROUND OF THE INVENTION

This invention relates to implantable electrical apparatus for stimulating body organs and has particular relationship to such apparatus which includes a catheter for connecting the electrical output of the apparatus to the organ to be stimulated. In the interest of dealing with this invention concretely so that it will be better understood by those skilled in the art, the description of this invention is predominately directed to heart pacers. While this invention is uniquely applicable to heart pacers, it is also applicable to other organ-stimulating apparatus and to the extent that it is embodied in such apparatus, such embodiment is within the scope of this invention.

A typical implantable organ-stimulating apparatus is a heart pacer of the type described in Purdy, et al. U.S. Pat. No. 3,866,616. Such a heart pacer includes a container within which an electrical circuit is sealed. This electrical circuit produces electrical pulses which stimulate the heart of the host. The stimulating pulses are supplied to the heart through a catheter connected between the circuit and the heart. The catheter has a terminal (or, in the case of a bi-polar pacer, a pair of terminals,) which is inserted laterally in a terminal block that communicates with a cavity. The terminal is held by a set-screw which passes through the cavity and is screwed into the terminal block and becomes cold welded to the terminal. To preclude electrical leakage through body fluids, the terminal block must be sealed against the penetration of body fluids. The seal is inserted in the cavity. The securing of the terminal of the catheter and the necessity of sealing the cavity has presented a serious problem to the surgeons who implant the heart pacers. To suppress the penetration of body fluids into the terminal block some surgeons adopted the practice of plugging the opening in the cavity in which the set-screw is inserted with a silicone-rubber cement during implantation. This expedient has not proven entirely satisfactory. Another practice which has been preferred is to plug the opening in the cavity with a silicone-rubber plug from whose periphery an O-ring extends. U.S. Pat. No. 4,037,277 granted July 26, 1977 to Frederick J. Shipko for Surgical Tool and assigned to CORATOMIC, INC. is directed to a heart pacer including a surgical tool for inserting the set-screw and the plug in this practice. While the Shipko teaching has materially improved the practice of securing the catheter terminal and sealing the cavity into which it extends, surgeons continue to experience difficulties in carrying out this operation. A source of frustration experienced by surgeons is that the set screw and plug are small and at times one or the other is lost on or near the operating table.

It is an object of this invention to overcome the above disadvantages of past practice in implanting heart pacers and other organ-stimulating apparatus and to provide such apparatus which shall include means for securing and sealing the catheter that shall include only a unitary securing and sealing component that shall lend itself to ready manipulation by the surgeon during an implantation. Another object of this invention is to provide a set screw having unique application to organ-stimulating apparatus but also having more general use.

SUMMARY OF THE INVENTION

In accordance with this invention, there is provided implantable organ-stimulating apparatus including an electrically-insulating set screw. The set screw includes a threaded member which extends from a head of insulating material into which it is molded. An O-ring extends about the periphery of the head. The head has a slot for insertion of a tool. By manipulation of the tool, the threaded member of the set screw is screwed through the cavity into the threaded terminal block in the organ-stimulating apparatus. The tip of the threaded member engages the catheter terminal and secures the catheter. The O-ring is compressed against the wall of the cavity sealing the cavity and the terminal block. The surgeon is thus provided with a unitary component which he can readily screw into the cavity in one operation securing the catheter and sealing the cavity. This invention not only eliminates the problems involved in possible loss of the plug or set screw, in prior art practice, but it also shortens the time taken in implanting the heart pacer or other organ-stimulating apparatus.

BRIEF DESCRIPTION OF THE DRAWING

For a better understanding of this invention, both as to its organization and as to its operation, together with additional objects and advantages thereof, reference is made to the following description taken in connection with the accompanying drawing, in which:

FIG. 1 is a view in top elevation taken in the direction of the arrow I of FIG. 2 of a heart pacer in accordance with this invention;

FIG. 2 is a fragmentary view in longitudinal section taken along line II—II of FIG. 1 but showing only the internal parts of the upper portion of the heart pacer;

FIG. 3 is a view in longitudinal section of the insulating set screw of the apparatus shown in FIGS. 1 and 2;

FIG. 4 is a view in side elevation of the threaded-member assembly of the set screw of the heart pacer shown in FIG. 1;

FIG. 5 is a plan view of the assembly shown in FIG. 4 taken in the direction of the arrow V in FIG. 4;

FIG. 6 is a plan view of the strengthening cap molded to the head of the set screw of the heart pacer shown in FIG. 1, taken in direction of the arrow VI of FIG. 7;

FIG. 7 is a view in section taken along line VII—VII of FIG. 6;

DETAILED DESCRIPTION OF THE INVENTION

Figure 8:
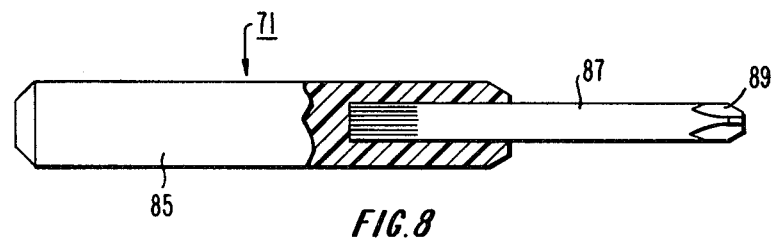
FIG. 8 is a view in side elevation of the tool for securing the set screw in the cavity of the heart pacer.

The apparatus shown in FIGS. 1 and 2 is a heart pacer 21. In FIGS. 1 and 2 only the top and the upper portion of the internal structure of the heart pacer 21 are shown. This showing is adequate for understanding of this invention. The pacer 21 shown in FIGS. 1 and 2 has a container 23 of the ovaloidal or ellipsoidal shape shown in U.S. Pat. No. 3,987,799. However, the heart pacer 21 as shown is of the type powered by a battery 25 within the container 23 whereas the pacer shown in U.S. Pat. No. 3,987,799 is powered by a radioactive source. The essential features of a battery-powered pacer are disclosed in U.S. Pat. No. 4,041,956 dated Aug. 16, 1977 to David L. Purdy, et al. for Pacemakers and assigned to CORATOMIC, INC.

The battery 25 is embedded in polyurethane foam 27. The casing of the battery has a lip 31 where it is seal welded. The battery 25 is connected to energize a solid-state circuit 35 from whose output a conductor 37 derives pulses for the heart. The conductor 37 is connected to a feed-through connector 39 through a feed-through assembly 41 sealed vacuum tight to the container 23. The feed-through assembly is generally similar to the assembly 264 of the heart pacer shown in FIG. 3 of U.S. Pat. No. 3,866,616. A shield 33 is provided for protecting the battery 25 and the circuit 35 from the laser beam by which the halves of the container 23 are welded. The feed-through connector 39 is connected, typically welded or soldered, to a terminal block 43. The block 43 in the form of a rectangular parallelepiped having an axial opening 46 along its length and a lateral hole 44 in opposite sides. The upper portion 48 of the wall of the axial opening 46 is threaded.

The portion of the feed-through assembly 41 above the container 23, the feed-through connector 39, and the terminal block 43 are encapsulated in a capsule 45 typically of EPOXY resin which is molded to the encapsulated components 41, 39, 43 and to the container 23. The capsule 45 is anchored by a loop 47 of wire which is spot welded to the outer surface of the container 23 where the capsule 45 is seated. Typically, the loop 47 is composed of titanium wire of 0.010 inch diameter. The capsule 45 has a central opening coaxial with the opening 44 in the terminal block 43. This opening tapers to a smaller diameter near the entrance side to the opening 44. The catheter 51 is inserted in this opening with its terminal 53 nesting in the attenuated end of the opening. The capsule 45 has an opening 55 which is coaxial and coextensive with the opening 46 in the terminal block 43. The opening 55 has a diameter typically approximately the same as the diagonal of the horizontal cross section of the terminal block 43. The opening 55 constitutes a cavity which communicates with the threaded portion 48 of the opening 46 within which the terminal 53 of the catheter 51 is secured. There is a transverse opening 56 in the capsule 45 for suturing the heart pacer 21 to the body of the host if necessary or desireable.

The terminal 53 is secured and also electrically connected to the terminal block 43, in accordance with this invention, by an electrically insulating set screw 61. This set screw 61 (FIGS. 3 and 4) includes a threaded member 63 and an insulating head 65. It is desireable that the threaded member 63 be of high strength and it is typically composed of a titanium alloy of 6% vanadium, 4% aluminum and the remainder titanium. The threaded member typically has an overall length of 0.187 inch and No. 2-56 thread. At its end the member 63 has a 30° taper to a tip. A rectangular slot, typically having a depth of 0.045 + 0.002 − 0.005 inch and a width about 0.025 inch, extends centrally across the top of the threaded member 63. A locking bar 67 nests centrally in the slot (FIGS. 3, 4, 5). Typically, the locking bar 67 is composed of titanium and has a length of 0.160 inch, a depth of 0.040 inch and a width of 0.020 inch. At its center the locking bar 67 is spot welded to the threaded member 63.

Figure 9:
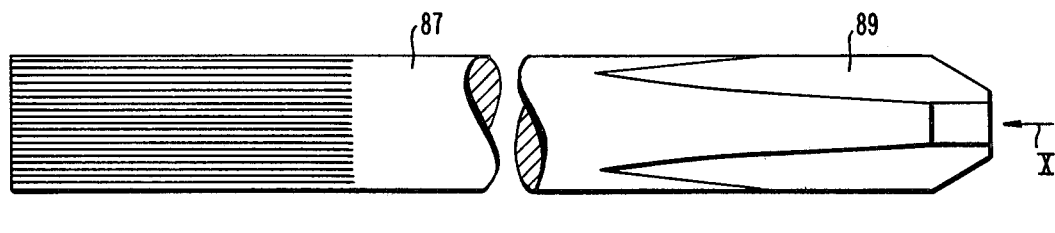
FIG. 9 is a view in side elevation of the head of the tool shown in FIG. 8.
Figure 10:
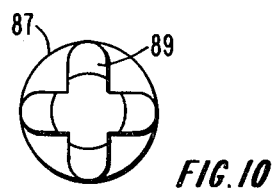
FIG. 10 is a view in end elevation in the direction of the arrow X of FIG. 9.

The electrically insulating head 65 (FIG. 3) is typically composed of C8 W795 HYSOL medical grade EPOXY resin. The head 65 is of circularly cylindrical shape and typically has a height of 0.158 inch and an overall diameter of 0.243 inch. Above its base the cap has a shoulder 66. Typically the shoulder 66 is about 0.025 inch above the base and has a width of 0.015 inch. The head 65 has a cruciform slot 69 in its top for engagement by a tool 71 (FIGS. 8, 9, 10) for screwing the set screw into the terminal block 43. The head 65 is strengthened against rupture, when it is screwed into the terminal block 43 by a cap 73 typically of 0.010 inch thick titanium (FIGS. 6 and 7). The cap 73 is of generally hollow circular cylindrical form but has a fillet typically of 0.025 inch radius at the top. A plurality of tabs 75 are formed in the cap by slitting the wall of the cap 73 in a plurality of symmetrically disposed positions and bending the slitted portions inwardly forming slots part way up the walls of the cap. The cap 73 has in its top a cruciform opening 77 of the same dimensions as the slot in the head 65. The center of this opening 77 is coaxial with the cap. Typically the cap 73 has a diameter of 0.242 inch and height of 0.108 inch. The bottom of the tabs 75 typically are 0.040 inch above the base of the cap 73. The arms 79 of the cruciform opening 77 have typically a width of 0.031 inch terminating at their outer ends in semi-circles of 0.031 inch diameter. The length of the arms 79 from the axis of the cap 73 is typically 0.050 inch.

The threaded member 63, the locking bar 67, the cap 73 and the head 65 are formed into a rigid unit by molding. The assembly of the threaded member 63 and locking bar 67 are first positioned in the mold. Next, the cap is positioned in the mold. The resin for the head 65 is then deposited in the mold and the necessary pressure and heat applied. Before the resin of the head 65 sets, the slot 69 is formed in the head by inserting a forming molding pin. In the insulating set screw 61, the head assembly as molded has a circular slot defined between the lower end of the cap 73 and the shoulder 66. Typically this slot has a height of 0.025 inch. Typically the tip of the threaded member is spaced about 0.122 inch below the base of the head 65; the overall length of the insulated set screw is 0.28 inch.

An O-ring 81 typically of Silastic silicone rubber MDX4-4515 is secured in the slot between the end of the head 65 and the shoulder 66. Typically the O-ring 81 is of annular shape having in cross section the form of a rectangle merging into a semi-circle. The inner surface 68 of the O-ring which in cross section is a side of the cross-section rectangle is of circularly cylindrical form. Typically the inner diameter of the O-ring 81 is 0.147 ± 0.002 inch and its outer diameter 0.191 ± 0.002 inch. The thickness of the O-ring 81 from the crown to the base of the cross-section rectangle is typically 0.025 inch and the cross-section rectangle has a width of 0.014 inch. The O-ring is snapped into the slot 66 with the inner surface 68 of the cross-section rectangle engaging the inner surface of the slot 66. Because of the inner surface or boundary 68 of the O-ring is flat an effective seal to the surface of the head 65 is formed. The diameter of the head 65 at the slot between the shoulder 66 and the cap 73 is 0.213 inch while the inner diameter of the O-ring 81 is 0.147 ± 0.002 inch. The O-ring is then tightly secured on the head 65. Since the shoulder is 0.015 inch, the O-ring extends outwardly of the head 65.

To screw in the set screw 61 the tool 71 (FIGS. 8, 9, 10) is provided. This tool has a handle 85 of ¼ inch diameter NYLON and a head 87 of stainless steel. The head 87 is secured in the handle 85. The overall length of the screw driver is typically 2.25 inches; the head 85 extends 0.75 inch from the handle. The tip 89 of the head 87 is formed to engage and mate with the walls of the slot 69. The tip 87 tapers from a diameter of 0.093 inch to a diameter of 0.050 inch along a 30° taper. Typically, the head 85 is 1.25 inches long and the tip has length of 0.30 inch.

In the practice of this invention the set screw 61 is screwed into the terminal block 43 (FIG. 2) so that the threaded member 63 engages firmly, and is ultimately welded to, the terminal 53. The tip of the threaded member 63 of the set screw 61 must be spaced from the base of the head 65 so that the tip is not precluded from engaging the terminal 53 by engagement of the head 65 with the top of the terminal block 43. Typically, the base of the head 65 should be about 0.020 inch above the top of the terminal block with the tip in engagement with terminal 53. The wall of the opening 55 in the head 65 of the pacer 21 has a diameter appreciably smaller than the outer diameter of the O-ring 81 so that the O-ring engages the wall tightly and seals the cavity, defined by this wall, tightly against the penetration of body fluids.

While a preferred embodiment of this invention has been disclosed herein, many modifications thereof are feasible. This invention is not to be restricted except insofar as is necessitated by the spirit of the prior art.

I claim:

1. Organ stimulating electrical apparatus to be implanted in a body including a catheter for connecting said apparatus to said organ of said body, said apparatus also including a threaded receptacle into which said catheter extends and a set screw for securing said catheter in said apparatus, the said set screw including:
   (a) a threaded member for screwing into the thread of said receptacle and engaging and securing said catheter,
   (b) an electrically-insulating head secured to said threaded member and,
   (c) resilient means secured in and extending about, the periphery of said head; said resilient means engaging the wall of said receptacle when said member is screwed into said receptacle to seal said receptacle against the penetration of body fluids.

2. The apparatus of claim 1 wherein the receptacle includes a terminal block through which the catheter extends and a cavity communicating with the terminal block, the terminal block being threaded, the threaded member being screwed into the terminal block and the resilient means engaging the wall of the cavity to seal the cavity and terminal block.

3. The apparatus of claim 1 wherein the insulating head has a metallic cap molded into the head to preclude fracture of the head.

4. The apparatus of claim 1 wherein the head has a groove engageable by a tool to screw the set screw into the receptacle and wherein a metallic cap is molded about the groove to preclude fracture of the head by the stress produced by the tool.

5. The apparatus of claim 1 wherein the resilient means is an O-ring whose inner surface that engages the head is circularly cylindrical.

6. Organ stimulating electrical apparatus to be implanted in a body including a catheter for connecting said apparatus to said organ of said body, said apparatus also including a threaded receptacle into which said catheter extends and a set screw for securing said catheter in said apparatus, the said set screw also including a threaded member for screwing into the thread of said receptacle and engaging and securing said catheter, an electrically-insulating head secured to said threaded member, resilient means secured to, and extending about, the periphery of said head, said resilient means engaging the wall of said receptacle when said member is screwed into said cavity to seal said cavity against the penetration of body fluids, and means, internally of said head, interconnecting said threaded member and said head and locking said member against turning in said head when said set screw is screwed into said receptacle.

7. The apparatus of claim 1 wherein the locking means includes a locking bar extending transversely through the threaded member, said bar being engaged by the insulating material of the head.

8. The apparatus of claim 7 wherein the head is molded about the threaded member and locking bar.

* * * * *